US007276065B2

United States Patent
Morley et al.

(10) Patent No.: US 7,276,065 B2
(45) Date of Patent: *Oct. 2, 2007

(54) MINIMALLY INVASIVE SURGICAL HOOK APPARATUS

(75) Inventors: Tracey A. Morley, Sunnyvale, CA (US); David S. Baron, Cupertino, CA (US); Daniel T. Wallace, Redwood City, CA (US)

(73) Assignee: Intuitive Surgical, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/581,311

(22) Filed: Oct. 16, 2006

(65) Prior Publication Data

US 2007/0038214 A1    Feb. 15, 2007

Related U.S. Application Data

(62) Division of application No. 10/235,063, filed on Sep. 4, 2002, now abandoned, which is a division of application No. 09/415,568, filed on Oct. 8, 1999, now Pat. No. 6,491,691.

(51) Int. Cl.
    *A61B 18/12* (2006.01)
(52) U.S. Cl. .......................... 606/41; 606/49
(58) Field of Classification Search ............ 606/1, 606/41–51; 607/96, 98–101
    See application file for complete search history.

(56) References Cited

U.S. PATENT DOCUMENTS

| 5,429,596 | A | 7/1995 | Arias |
| 5,792,135 | A | 8/1998 | Madhani et al. |
| 5,797,900 | A | 8/1998 | Madhani et al. |
| 6,090,120 | A | 7/2000 | Wright et al. |
| 6,110,170 | A | 8/2000 | Taylor |

OTHER PUBLICATIONS

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

*Primary Examiner*—Roy D. Gibson
*Assistant Examiner*—Aaron Roane

(57) ABSTRACT

A cautery hook includes a proximal portion, a shank portion, and a distal hook portion. The shank portion is connected to the proximal portion at a bent knee protruding generally on a front side of the cautery hook. The distal hook portion is connected to the shank portion at an ankle protruding generally on a rear side of the cautery hook opposite from the front side of the cautery hook. The distal hook portion includes a distal hook tip generally on the front side of the cautery hook. The bent knee, ankle, and distal hook tip are the three most likely locations of contact between the cautery hook and a cannula sleeve when the cautery hook is passed through the cannular sleeve between an internal surgical site and the outside. Each contact tends to self-align the cautery hook to allow the hook to pass through the cannula sleeve without getting stuck or damaged.

12 Claims, 9 Drawing Sheets

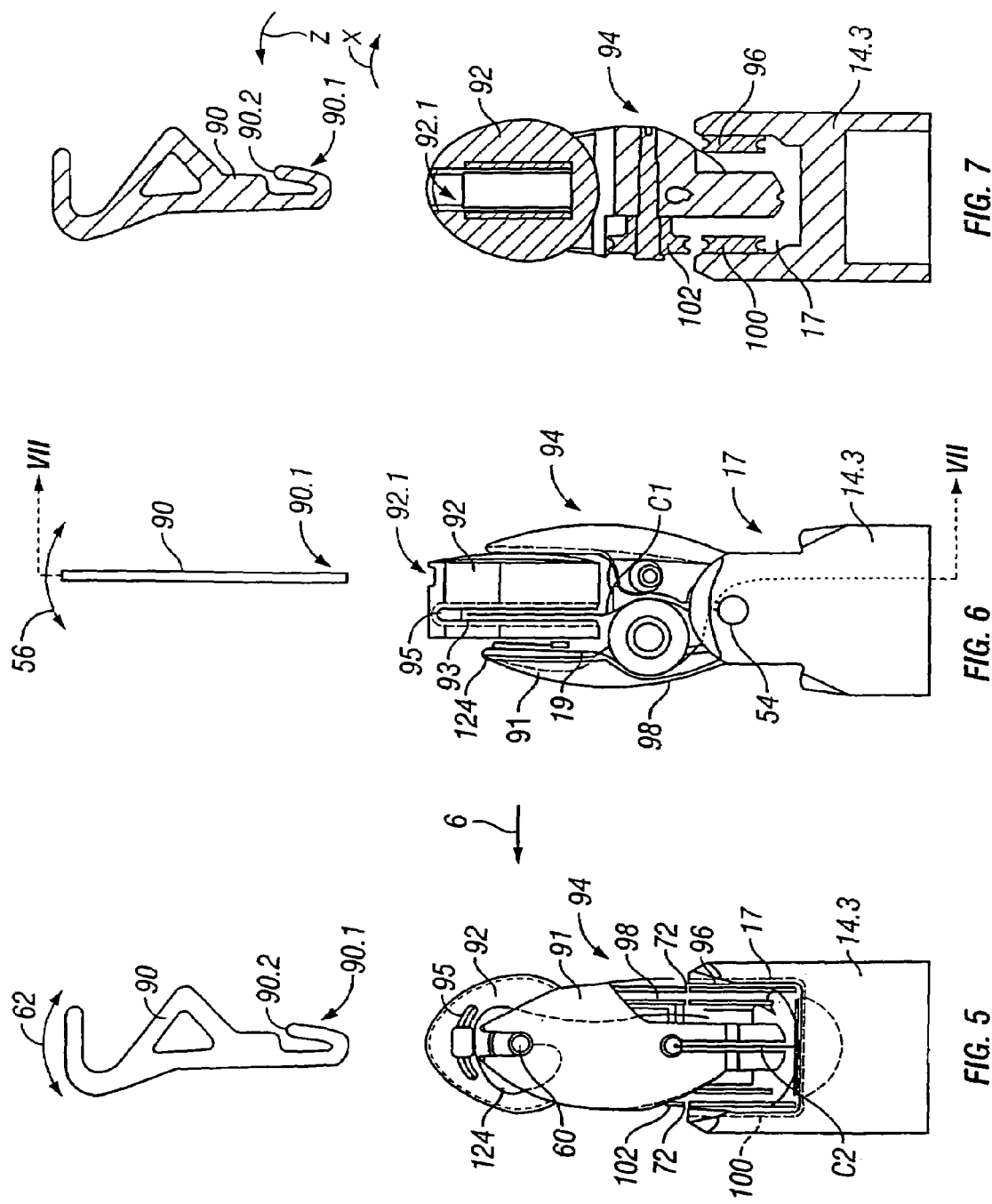

MINIMALLY INVASIVE SURGICAL HOOK APPARATUS

CROSS-REFERENCES TO RELATED APPLICATIONS

This application is a divisional of prior application Ser. No. 10/235,063 entitled "Minimally Invasive Surgical Hook Apparatus and Method for Using Same" by Morley et al., filed 4 Sep. 2002, now abandoned and which is a divisional of prior application Ser. No. 09/415,568 issued as U.S. Pat. 6,491,691 and entitled "Minimally Invasive Surgical Hook Apparatus and Method for Using Same" by Morley et al., filed 8 Oct. 1999. This application claims the benefit of these prior applications, which are incorporated by reference.

BACKGROUND OF THE INVENTION

Advances in minimally invasive surgical technology could dramatically increase the number of surgeries performed in a minimally invasive manner. Minimally invasive medical techniques are aimed at reducing the amount of extraneous tissue that is damaged during diagnostic or surgical procedures, thereby reducing patient recovery time, discomfort, and deleterious side effects. The average length of a hospital stay for a standard surgery may also be shortened significantly using minimally invasive surgical techniques. Thus, an increased adoption of minimally invasive techniques could save millions of hospital days, and millions of dollars annually in hospital residency costs alone. Patient recovery times, patient discomfort, surgical side effects, and time away from work may also be reduced with minimally invasive surgery.

The most common form of minimally invasive surgery may be endoscopy. Probably the most common form of endoscopy is laparoscopy, which is minimally invasive inspection and surgery inside the abdominal cavity. In standard laparoscopic surgery, a patient's abdomen is insufflated with gas, and cannula sleeves are passed through small (approximately ½ inch) incisions to provide entry ports for laparoscopic surgical instruments. The laparoscopic surgical instruments generally include a laparoscope (for viewing the surgical field) and working tools. The working tools are similar to those used in conventional (open) surgery, except that the working end or end effector of each tool is separated from its handle by an extension tube. As used herein, the term "end effector" means the actual working part of the surgical instrument and can include clamps, graspers, scissors, staplers, and needle holders, for example. To perform surgical procedures, the surgeon passes these working tools or instruments through the cannula sleeves to an internal surgical site and manipulates them from outside the abdomen. The surgeon monitors the procedure by means of a monitor that displays an image of the surgical site taken from the laparoscope. Similar endoscopic techniques are employed in, e.g., arthroscopy, retroperitoneoscopy, pelviscopy, nephroscopy, cystoscopy, cisternoscopy, sinoscopy, hysteroscopy, urethroscopy and the like.

Minimally invasive telesurgical robotic systems are being developed to increase a surgeon's dexterity when working within an internal surgical site, as well as to allow a surgeon to operate on a patient from a remote location. In a telesurgery system, the surgeon is often provided with an image of the surgical site at a computer workstation. While viewing a three-dimensional image of the surgical site on a suitable viewer or display, the surgeon performs the surgical procedures on the patient by manipulating master input or control devices of the workstation. The master controls the motion of a servomechanically operated surgical instrument. During the surgical procedure, the telesurgical system can provide mechanical actuation and control of a variety of surgical instruments or tools having end effectors such as, e.g., tissue graspers, needle drivers, or the like, that perform various functions for the surgeon, e.g., holding or driving a needle, grasping a blood vessel, or dissecting tissue, or the like, in response to manipulation of the master control devices.

An electrosurgical instrument is an end effector for coagulating ruptured blood vessels or the like. The instrument typically includes an electrode that applies current to living tissue at a surgical site. As the tissue current is conducted through the tissue, the tissue temperature rises, ultimately causing desiccation, cutting, and/or coagulation of the target tissue or vessel. Some cautery instruments include a J-shaped or L-shaped distal hook conveniently configured to snag or capture anatomical tissue such as a blood vessel for cauterization. The J-shaped or L-shaped hook often includes a distal hook portion connected to a substantially straight shank portion. The lateral dimension of the hook portion typically is substantially larger than that of the shank portion. When the cautery hook is passed through a cannula sleeve between the internal surgical site and the outside, the hook portion may get caught at an edge of the cannula sleeve or become stuck in the sleeve, particularly if the hook portion includes a sharp tip. In some cases, the hook portion may even break off when passing through the cannula sleeve.

SUMMARY OF THE INVENTION

The present invention is generally directed to robotic surgery methods, devices, and systems. The invention provides a cautery hook that is configured to substantially avoid being caught inside a cannula sleeve and being damaged or broken when the cautery hook is passed through the cannula sleeve.

In accordance with an aspect of the present invention, a cautery hook includes a proximal portion having a proximal end. A shank portion is connected to the proximal portion at a bent knee protruding generally on a front side of the cautery hook. A distal hook portion includes a distal hook tip generally on the front side of the cautery hook. The distal hook portion is connected to the shank portion at an ankle protruding generally on a rear side of the cautery hook opposite from the front side of the cautery hook.

In use, the bent knee, ankle, and distal hook tip are the three most likely locations of contact between the cautery hook and a cannula sleeve when the cautery hook is passed through the cannular sleeve between an internal surgical site and the outside. Each location of contact tends to self-align the cautery hook to allow the hook to pass through the cannula sleeve without getting stuck or damaged.

In some preferred embodiments, a proximal portion line extending generally between the proximal end and the bent knee is angularly spaced from a shank portion line extending generally between the bent knee and the ankle by a bent knee angle generally on the front side of the cautery hook. The bent knee angle is greater than 180° and no greater than about 270°. In a specific embodiment, the bent knee angle is between about 200° and about 250°.

In some preferred embodiments, the distal hook tip coincides with, or is disposed rearward of, a proximal portion plane which extends from the proximal end toward the bent knee and which is generally transverse to a distal hook plane on which the distal hook portion lies.

In some preferred embodiments, a distal hook tip tangent which is generally tangential to the distal hook portion at the distal hook tip is angularly spaced by a master angle from a proximal portion line extending between the proximal end and the bent knee. The master angle is disposed generally on the front side of the cautery hook, and is greater than 90°, preferably between about 110° and about 180°, and more preferably between about 120° and about 150°.

In a preferred embodiment, a rear support is disposed rearward of the bent knee and extends generally between the proximal end and the ankle.

In another preferred embodiment, the bent knee is spaced from the ankle by a shank portion length and the ankle is spaced from the distal hook tip by a distal hook portion length. The shank portion length is approximately equal to or greater than the distal hook portion length.

In specific embodiments, the distal hook portion is generally linear. The proximal portion, the shank portion, and the distal hook portion are generally planar and generally coplanar with each other. The proximal portion includes an engagement base at the proximal end for coupling the cautery hook to a support shaft.

In accordance with another aspect of the invention, a cautery hook includes a generally linear proximal portion. A generally linear shank portion is connected to the proximal portion at a bent knee. The shank portion is generally coplanar with the proximal portion. A generally linear distal hook portion includes a distal hook tip and is connected to the shank portion at an ankle. The distal hook portion is generally coplanar with the shank portion. The distal hook tip and the bent knee are disposed generally on a front side of the cautery hook and the ankle is disposed generally on a rear side of the cautery hook which is opposite from the front side.

In some preferred embodiment, the distal hook portion is angularly spaced by a master angle from the proximal portion. The master angle is disposed generally on the front side of the cautery hook, and is greater than 90°.

In accordance with another aspect of the invention, a cautery hook configured to self-align when passed through a cannula sleeve includes a distal hook portion having a distal hook tip disposed generally on a front side of the cautery hook. The cautery hook further includes a proximal end. A protruding portion is formed between the proximal end and the distal hook portion. The protruding portion includes a protruding surface generally on the front side of the cautery hook.

In some preferred embodiments, the bent knee generally coincides with, or protrudes generally forward of, a plane extending between the proximal end and the distal hook tip. The cautery hook further includes an ankle formed between the bent knee and the distal hook tip. The ankle protrudes generally on the rear side of the cautery hook. The protruding portion is formed between a proximal portion extending from the protruding portion to the proximal end and a shank portion extending from the protruding portion to the ankle.

Another aspect of the invention is directed to a system for cauterizing a target tissue in an internal surgical site of a patient body. The system includes a cannula sleeve having a proximal end, a distal end, and a lumen therebetween. The distal end is insertable into the patient body for accessing the internal surgical site through the lumen. A tool extends into the lumen of the cannula sleeve. The tool includes a cautery hook coupled with a shaft by a joint. The cautery hook has a tip supported by a bend so that the tip extends in a forward direction. A surface of the cautery hook is disposed proximally of the bend and extends forward sufficiently that sliding engagement between the proximal hook surface and the lumen of the cannula sleeve aligns the cautery hook with the shaft so as to inhibit interference between the tip and the distal end of the cannula sleeve when the cautery hook moves proximally into the cannula sleeve. The tool may be a robotic tool.

In some preferred embodiments, the bend of the cautery hook is generally planar. The cautery hook is rotatable generally on a plane of rotation relative to the shaft at a pivotal connection with the bend lying generally on the plane of rotation. The proximal cautery surface generally coincides with, or extends generally forward of, a plane which is perpendicular to the plane of rotation and extends between the pivotal connection and the tip.

BRIEF DESCRIPTION OF THE DRAWINGS

FIG. 5 is a front view of a wrist mechanism for a cautery hook in accordance with a preferred embodiment of the invention;

FIG. 6 is a side view of the wrist mechanism of FIG. 5 in the direction of arrow VI;

FIG. 7 is a sectional view of the wrist mechanism of FIG. 5 along arrows VII-VII;

DESCRIPTION OF THE PREFERRED EMBODIMENTS

As used herein, the terms "cautery" and "cauterize" are used to describe delivery of electricity to tissue to heat the tissue as well as heating to burn/seal tissue. Therefore, cautery instruments as used herein include electrosurgical instruments.

Figure 1:
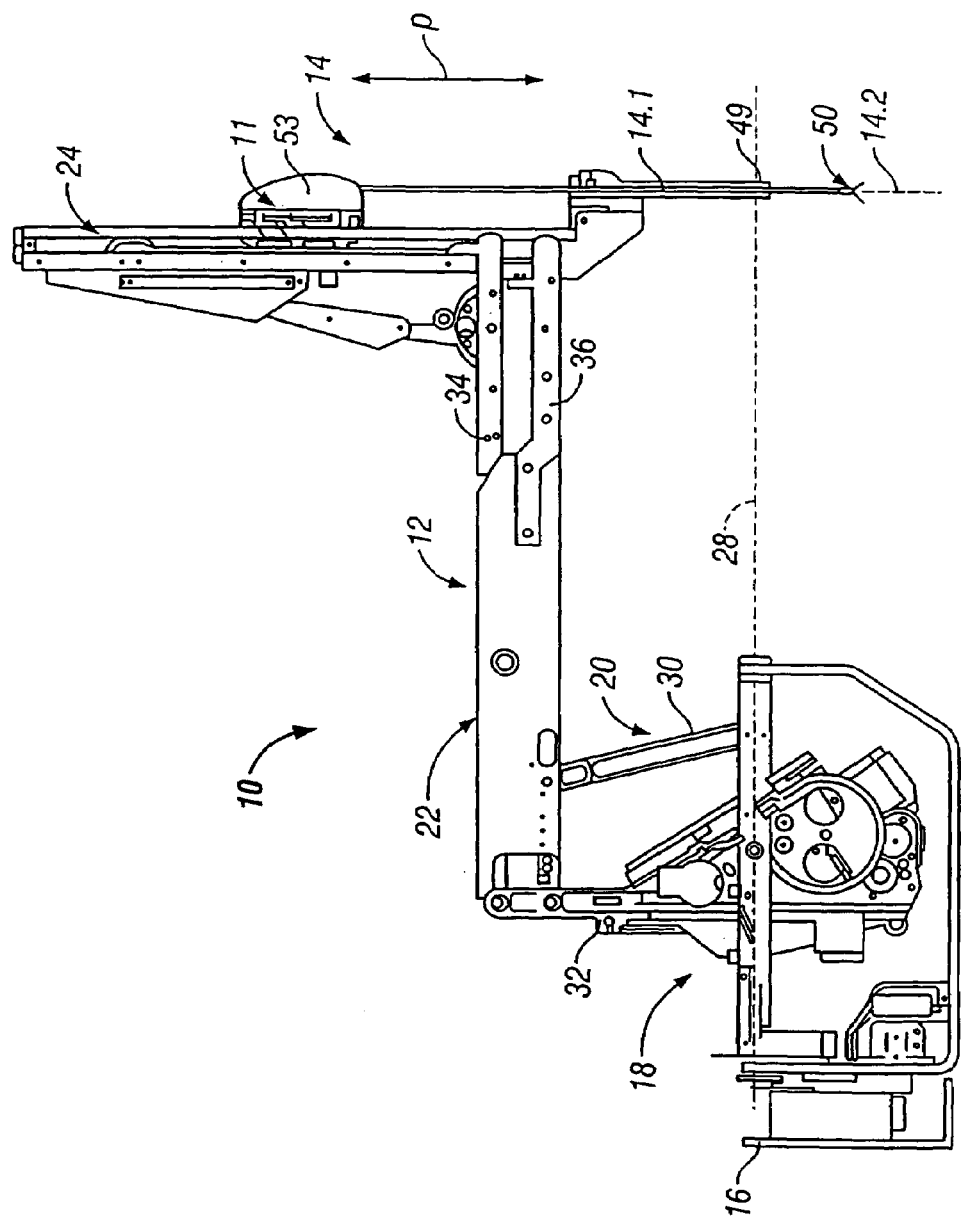
FIG. 1 is a side view of a robotic arm and surgical instrument assembly according to a preferred embodiment of the invention.
Figure 2:
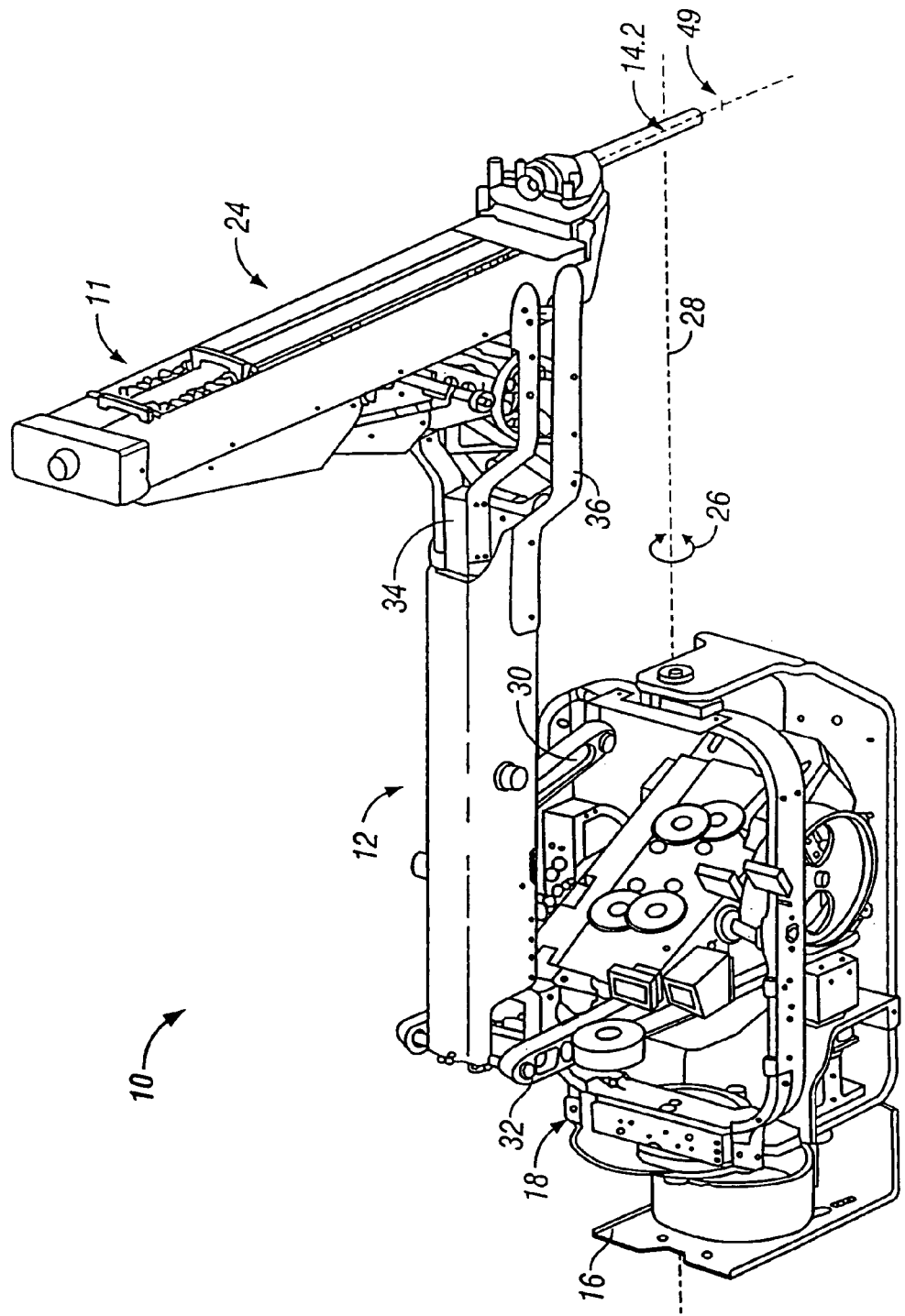
FIG. 2 is a perspective view of the robotic arm and surgical instrument assembly of FIG. 1.
Figure 3:
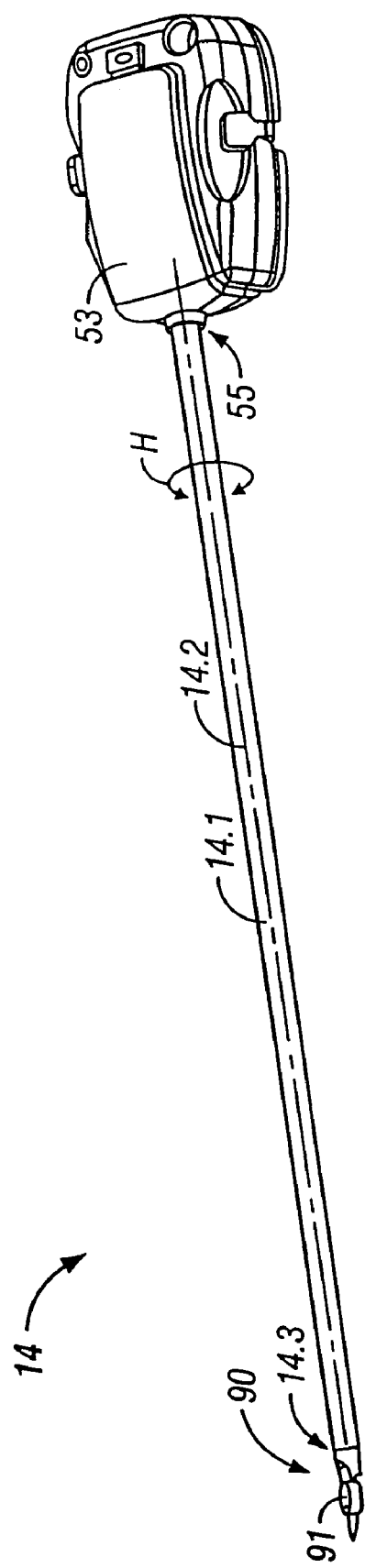
FIG. 3 is a perspective view of a surgical instrument according to a preferred embodiment of the invention.

FIGS. 1 and 2 illustrate a robotic arm and surgical instrument assembly 10. The assembly 10 includes a robotic arm 12 and a surgical instrument 14. FIG. 3 indicates the general appearance of the surgical instrument 14.

The surgical instrument 14 includes an elongate shaft 14.1. A wrist-like mechanism 94 is located at a working end of the shaft 14.1. A housing 53 arranged releasably to couple the instrument 14 to the robotic arm 12 is located at an opposed end of the shaft 14.1. In FIG. 1, and when the instrument 14 is coupled or mounted on the robotic arm 12, the shaft 14.1 extends along an axis indicated at 14.2. The instrument 14 is typically releasably mounted on a carriage 11 which is preferably driven to translate along a linear guide formation 24 in the direction of arrows P. The surgical instrument 14 is described in greater detail herein below.

The robotic arm 12 is typically mounted on a base (not shown) by means of a bracket or mounting plate 16. The base is typically in the form of a mobile cart or trolley (not shown) which is retained in a stationary position during a surgical procedure.

The robotic arm 12 includes a cradle 18, an upper arm portion 20, a forearm portion 22, and the guide formation 24. The cradle 18 is pivotally mounted on the plate 16 in a gimbaled fashion to permit rocking movement of the cradle in the direction of arrows 26 about a pivot axis 28, as shown in FIG. 2. The upper arm portion 20 includes link members 30, 32 and the forearm portion 22 includes link members 34, 36. The link members 30, 32 are pivotally mounted on the cradle 18 and are pivotally connected to the link members 34, 36. The link members 34, 36 are pivotally connected to the guide formation 24. The pivotal connections between the link members 30, 32, 34, 36, the cradle 18, and the guide formation 24 are arranged to enable the robotic arm to move in a specific manner.

Figure 4:
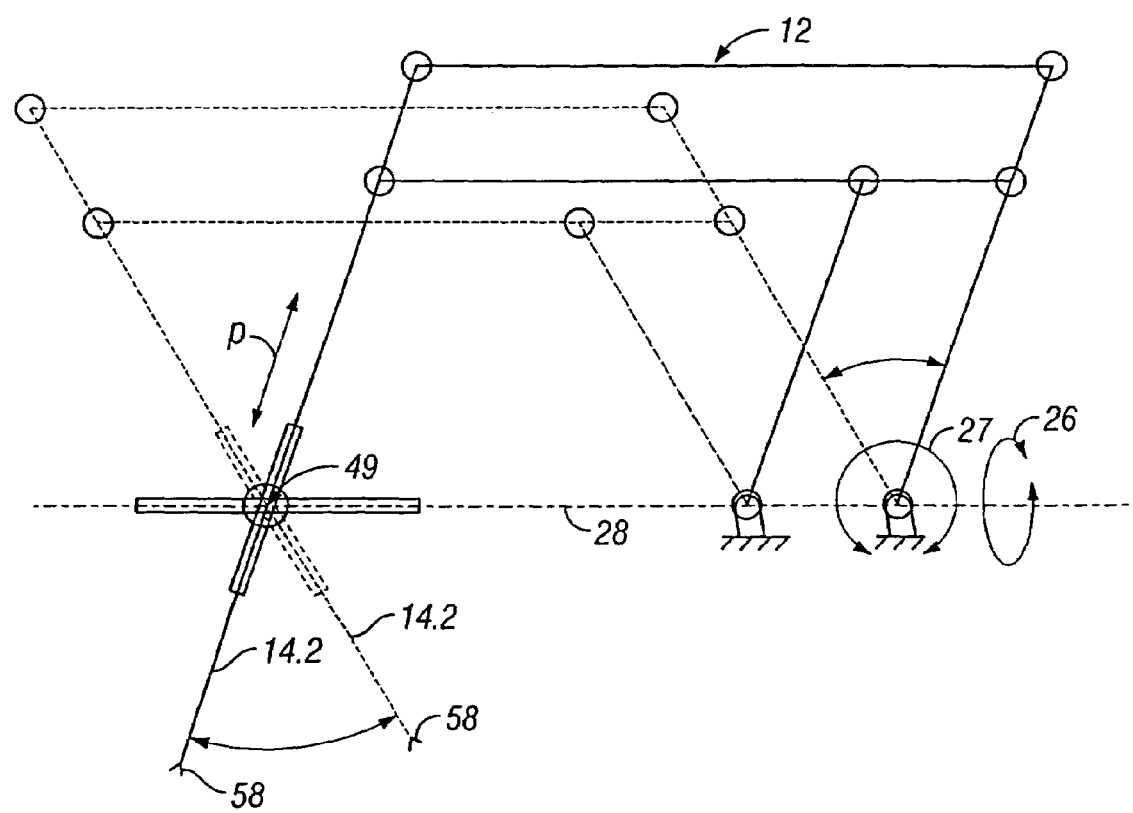
FIG. 4 is a schematic kinematic diagram corresponding to the side view of the robotic arm shown in FIG. 1, and indicates the arm having been displaced from one position into another position.

The movements of the preferred robotic arm 12 is illustrated schematically in FIG. 4. The solid lines schematically indicate one position of the robotic arm and the dashed lines indicate another possible position into which the arm can be displaced from the position indicated in solid lines.

It will be understood that the axis 14.2 along which the shaft 14.1 of the 30 instrument 14 extends when mounted on the robotic arm 12 pivots about a pivot center or fulcrum 49. Thus, irrespective of the movement of the robotic arm 12, the pivot center 49 normally remains in the same position relative to a stationary cart on which the arm 12 may preferably be mounted. In use, the pivot center 49 is positioned at a port of entry into a patient's body when an internal surgical procedure is to be performed. It will be appreciated that the shaft 14.1 extends through such a port of entry, the wrist-like mechanism 94 then being positioned inside the patient's body. Thus, the general position of the mechanism 94 relative to the surgical site in a patient's body can be changed by movement of the arm 12. Since the pivot center 49 is coincident with the port of entry, such movement of the arm does not excessively effect the surrounding tissue at the port of entry. It is to be appreciated that the invention is not limited to this particular arrangement and the field of application of the invention is not limited to surgical procedures at internal surgical sites only, but can be used on open surgical sites as well.

As can best be seen in FIG. 4, the preferred robotic arm 12 provides three degrees of freedom of movement to the surgical instrument 14 when mounted thereon. These degrees of freedom of movement are firstly the gimbaled motion indicated by arrows 26, pivoting or pitching movement as indicated by arrows 27, and the linear displacement in the direction of arrows P. Movement of the arm as indicated by arrows 26, 27 and P is controlled by appropriately positioned actuators, e.g., electrical motors or the like, which respond to inputs from its associated master control to drive the arm 12 to a desired position as dictated by movement of the master control.

Referring now to FIGS. 5-7, in which like reference numerals are used to designate similar parts unless otherwise stated, an end effector in the form of a cautery hook 90 is indicated. The hook 90 preferably is removably mountable on a single pulley arrangement 92. The pulley arrangement 92 forms part of the wrist mechanism 94. The wrist mechanism 94 has single pulleys 96, 98, 100, 102.

The wrist-like mechanism 94 includes a rigid wrist member 91. One end portion of the wrist member 91 is pivotally mounted in a clevis 17 on the end 14.3 of the shaft 14.1 by means of a pivotal connection 54. As best seen in FIG. 6, the wrist member 91 can pivot in the direction of arrows 56 about the pivotal connection 54.

The hook 90 is detachably coupled to the single pulley arrangement 92, which is pivotally mounted in a clevis 19 on an opposed end of the wrist member 91, by means of a pivotal connection 60. As a result, the hook 90 is angularly displaceable about the pivotal connection 60 as indicated by arrows 62 in FIG. 5.

In the specific embodiment shown, the hook 90 has an engagement portion 90.1. The engagement portion 90.1 is removably insertable into a slot 92.1 defined in the pulley arrangement 92. It will be appreciated that when the engagement portion 90.1 of the hook 90 is inserted into the slot 92.1, a free end 90.2 of the engagement portion 90.1 is marginally and resiliently bent in the direction of arrow Z as shown in FIG. 7. Once inserted, and when the hook 90 is urged to be removed from the slot 92.1, frictional engagement of the end 90.2 against an inner wall of the slot 92.1 tends to urge the free end 90.2 in an outward direction as indicated by arrow X, thus locking the engagement portion 90.1 in the slot 92.1. Locking the hook 90 in a mounted condition on the pulley arrangement 92 is important so as to inhibit the hook 90 from becoming dismounted from the pulley arrangement 92 during a surgical procedure. However, when removed from the surgical site, the hook 90 can be removed when a sufficient pulling force is applied so as to overcome the frictional locking action in the slot 92.1.

As best seen in FIG. 6, the single pulley arrangement 92 defines a circumferentially extending channel 93 in which an elongate element in the form of, e.g., an activation cable C1, is carried. A cable seat 95 defines a generally circumferentially directed hole generally in register with the circumferentially extending channel 93.

In use, the activation cable C1 extends through the cable seat 95, and has a thickened crimped portion along its length which seats against the larger side of the hole in the cable seat 95. The rest of the activation cable C1 extends along the channel 93 in opposed directions. The thickened portion is seated into position in the hole of the seat 95 so as to anchor the cable C1 in the hole.

As best seen in FIG. 5, the wrist member 91 is flanked by two pulleys 96, 100 which are coaxially positioned on the pivotal connection 54 and in the clevis 17 at the end 14.3 of the shaft 14.1. The other two pulleys 98, 102 are rotatably mounted on opposed sides of the wrist member 91. The pulley 98 is generally co-planar with its associated pulley 96, and the pulley 102 is generally co-planar with its associated pulley 100. Furthermore, each of the pulleys 98, 102 is positioned such that its circumference is in close proximity to the circumference of its associated pulley 96, 100, respectively. Thus, the circumferentially extending channel formation of each of the pulley 98, 102 and that of each of their associated pulleys 96, 100, respectively, define between them a space 72 through which the activation cable C1 can snugly pass. The cable C1 rides over the pulleys 100, 102, over part of circumferential channel 93 of the pulley arrangement 92, through the hole in the cable seat 95, again along part of the circumferential channel 93 of the pulley arrangement 92, and over the pulleys 98, 96.

It will be appreciated that the electrocautery instrument 14 is used to generate an electrical current at a surgical site so as to burn or seal, e.g., ruptured blood vessels. In use, the patient is earthed and a voltage is supplied to the electrode 90. An electrically conductive cable 124 extends from a plug on the housing 53 to the electrode 90. This conductive cable, or cautery wire, preferably includes a "service loop" around the distal joint axis 60, as shown in FIGS. 5 and 6. This service loop single, loose wrap around the joint permits rotation of the electrode 90 about the axis without placing undue stress or stretch on the wire during such rotation.

Other elongate elements, e.g., cables, are used to effect additional movement of the wrist mechanism 94. For example, an activation cable C2 as shown in FIG. 5 moves the wrist member 91 to pivot relative to the pivotal connection 54 in the direction of arrows 56 (FIG. 6). The cables C1, C2 pass from the wrist mechanism 94 through appropriately positioned holes in the base region of the clevis 17, and internally along the shaft 14.1, toward the housing 53 (FIG. 3). The apparatus for operating the wrist mechanism 94 are described in greater detail in U.S. application Ser. No. 09/398,958, entitled "Surgical Tools for Use in Minimally Invasive Telesurgical Applications", filed on Sep. 17, 1999.

Figure 8:
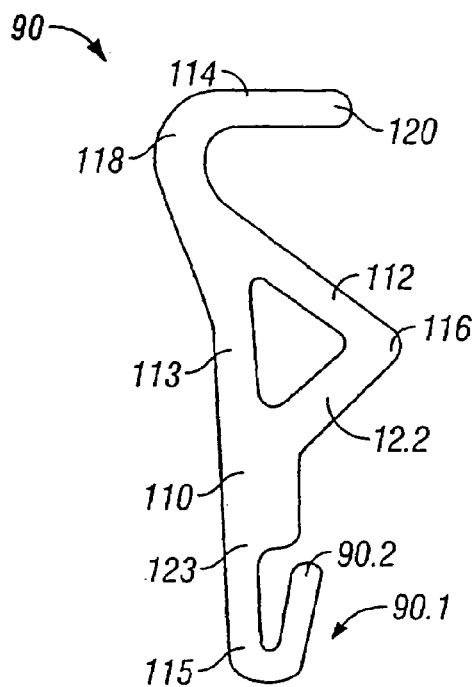
FIG. 8 is a side view of a cautery hook in accordance with a preferred embodiment of the invention.
Figure 9:
FIG. 9 is a front view of the cautery hook of FIG. 8.

As shown in FIGS. 8 and 9, the cautery hook 90 includes a proximal portion 110, a shank portion 112, and a distal hook portion or foot portion 114. The proximal portion 110 includes the engagement portion 90.1. The proximal portion 110 is connected to the shank portion 112 to define a bent knee 116 which is disposed generally on a front side of the cautery hook 90. The shank portion 112 is connected to the hook portion 114 to define an ankle 1 18 which is disposed generally on a rear side of the cautery hook 90. The hook portion 114 has a hook tip 120 disposed generally on the front side of the cautery hook 90. In the embodiment shown, the proximal portion 110, shank portion 112, and hook portion 114 are generally planar and generally uniform in thickness, and they are generally coplanar with each other. The hook portion 114 is generally linear. The cross-section of the hook 90 is generally flat and uniform in a preferred embodiment.

In this embodiment, the distal hook tip 120 coincides with, or is generally rearward of, a proximal portion plane which extends from the proximal end 115 toward the knee 116 and which is generally transverse to a distal hook plane on which the distal hook portion 114 lies. That is, the knee 116 coincides with, or extends generally forward of, a plane extending between the proximal end 115 and the hook tip 120. In this way, the distal hook tip 120 falls within the shadow of the knee 116 which shields the tip 120, and substantially prevents the tip 120 from being caught in a cannula sleeve and reducing the risk of breakage. Furthermore, the bent knee 116 is spaced from the ankle 118 by a shank portion length. The ankle 118 is spaced from the distal hook tip 120 by a hook portion length. In some preferred embodiments, the shank portion length is approximately equal to or greater than the hook portion length.

Figure 8A:
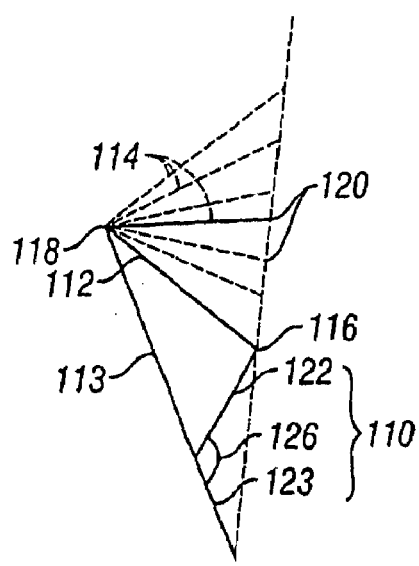
FIG. 8A is a simplified schematic view illustrating alternate embodiments of the cautery hook of FIG. 8.

FIG. 8A illustrate schematically alternate embodiments of the hook 90 by varying the angle of the hook portion 114 with respect to the proximal portion 110. As long as the distal tip 120 is shielded by the knee 116 (by coinciding with or being disposed rearward of the proximal portion plane), the hook portion 114 may be oriented in a wide range of angles while maintaining the distal tip 120 generally on the front side of the hook 90. The maximum length of the hook portion 114 between the ankle 118 and the tip 120 is shortest when the hook portion 114 is perpendicular to the proximal portion plane.

As shown in FIG. 8, the hook 90 advantageously includes a rear support 113 extending between the proximal end 115 and the ankle 118 to protect the backside of the knee 116 and the ankle 118 from being caught in a cannula sleeve. Without this rear support 113, the ankle would have to be angled so as to avoid interfering with a cannula distal portion during withdrawal from the surgical site, as is addressed for the embodiment shown in FIGS. 10-11.

The proximal portion 110 includes a forward branch or extension 122 which makes an angle 126 with the trunk 123, as shown in FIG. 8A. If the angle 126 is greater than about 90°, the knee 116 will aid in aligning the hook to prevent the front side of the proximal portion 110 from being caught in a cannula sleeve. The angle 126 is typically between about 110° and about 180°, more preferably between about 120° and about 150°.

Figure 10:
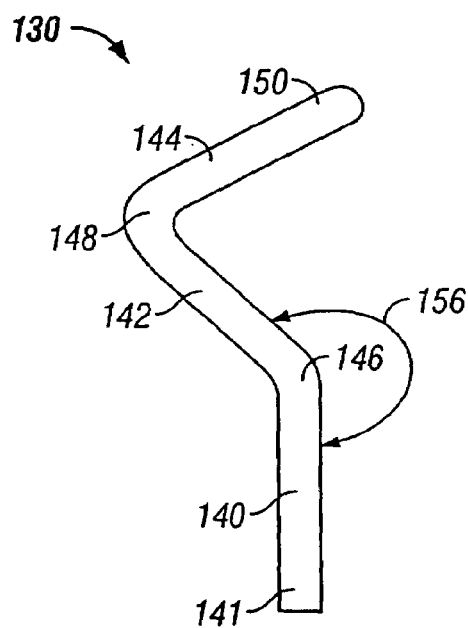
FIG. 10 is a side view of a cautery hook in accordance with another embodiment of the invention.
Figure 11:
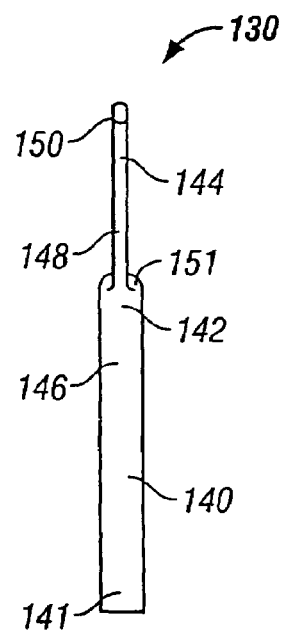
FIG. 11 is a front view of the cautery hook of FIG. 10.

FIGS. 10 and 11 show another cautery hook 130 including a proximal portion 140 with a proximal end 141, a shank portion 142, and a distal hook portion 144. The proximal portion 140 is connected to the shank portion 142 to define a bent knee 146 which is disposed generally on a front side of the cautery hook 130. The shank portion 142 is connected to the hook portion 144 to define an ankle 148 which is disposed generally on a rear side of the cautery hook 130. The hook portion 144 has a hook tip 150 disposed generally on the front side of the cautery hook 130. A bent knee angle 156 is formed between the proximal portion 140 and the shank portion 142, and is greater than 180°. In the embodiment shown, the proximal portion 140, shank portion 142, and hook portion 144 are generally linear portions, and are generally coplanar with each other. An engagement portion similar to the portion 90.1 shown in FIG. 8 may be attached to the proximal portion 140.

Figure 10A:
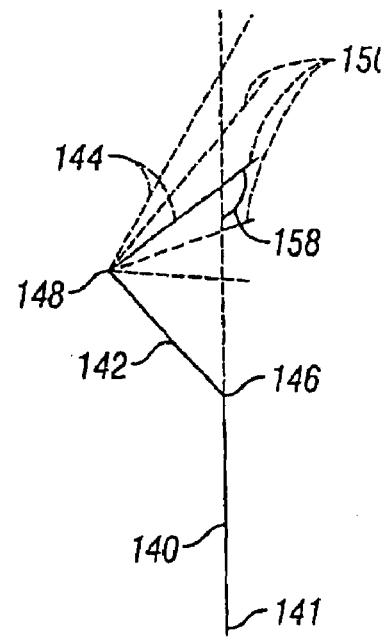
FIG. 10A is a simplified schematic view illustrating alternate embodiments of the cautery hook of FIG. 10.

In this embodiment, the hook portion 144 makes an angle 158 with a proximal portion line extending between the proximal end 141 and the knee 146 which is greater than about 90°, as illustrated in FIG. 10A. If this master angle 158 is equal to or less than about 90°, the distal tip 150 will tend to get caught in a cannula sleeve unless it is shielded by the knee 146 as in FIG. 8A. When the angle 158 increases beyond about 90°, the tendency of catching the tip 150 in a cannula sleeve decreases, even without shielding from the knee 146. The hook portion length between the ankle 148 and the tip 150 may be greater than (as well as smaller than or equal to) the shank portion length between the knee 146 and the ankle 148. Typically, the master angle 158 is between about 110° and 180°. In preferred embodiments, the master angle 158 is between about 120° and 150°. FIG. 10A likewise depicts a knee angle 156 that results in the shank portion 142 having an angle (equal to 360° minus angle 156) of greater than 90°, preferably greater than about 110°. This angular positioning of the shank portion 142 permits the ankle to self-align upon contacting a cannula distal tip, for example.

Figure 10B:
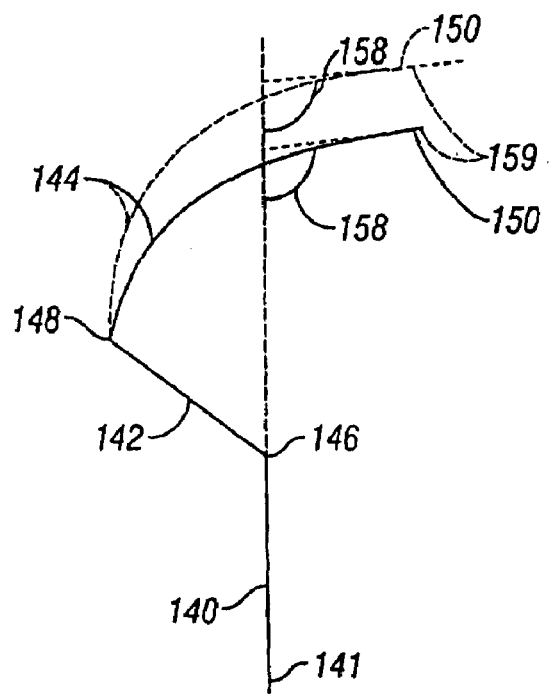
FIG. 10B is a simplified schematic view illustrating additional alternate embodiments of the cautery hook of FIG. 10.

FIG. 10B shows additional alternate embodiments in which the hook portion 144 is not linear but curved. Further, the ankle 148 in FIG. 10B could be eliminated by providing for a curved surface between the knee 146 and ankle 148. In any event, as long as the knee 146 protects the distal hook tip 150 from the cannula, the lack of an ankle or curvature of certain of the hook portions is within the scope of the invention. However, if the distal hook tip is not protected, then the master angle should be of the magnitudes described previously. That is, for these embodiments, the master angle 158 is more appropriately defined based on a distal hook tip tangent 159 which is generally tangential to the hook portion 144 at the distal hook tip 150. The master angle 158 is the angle measure from the proximal portion 140 extending between the proximal end 141 and the bent knee 146 to the distal hook tip tangent 159. The master angle 158 is greater than 90°, typically between about 110° and 180°, more preferably between about 120° and 150°.

The bent knee angle 156 is greater than 180° and more typically is greater than about 200°. The hook 130 in FIG. 10 does not include a rear support (such as the support 113 in FIG. 8) extending between the proximal end 141 and the ankle 148 to protect the backside of the knee 146 from being caught in a cannula sleeve. To avoid catching the cannula sleeve, the bent knee angle 156 between the proximal portion 140 and the shank portion 142 should typically be no greater than about 270°, and more preferably no greater than about 250°.

As shown in FIG. 11, the hook 130 in a preferred embodiment has a round proximal cross-section extending from the proximal end 141 to a region 151 in the shank portion 142 between the knee 146 and the ankle 148. A preferred diameter is about 0.06 inch. The distal cross-section extending from the region 151 to the distal tip 120 is generally slightly flattened (e.g., about 0.05 inch thickness) with corners that facilitate easier cutting over a round cross-sectional instrument.

A round distal cross-section is preferred for an electrosurgical instrument using RF (radiofrequency) current because of the uniformly dense current across the skin or surface area of the instrument. For a flat, rectangular cross-section as in the embodiments shown in FIGS. 8-11, the current is concentrated at the corners so that the hooks are better suited for cutting tissue than rounded hooks, although they do not coagulate as well because of the nonuniform concentration of current and the general sharpness of a generally flat hook of, e.g., 15 thousandths of an inch thick.

Figure 11A:
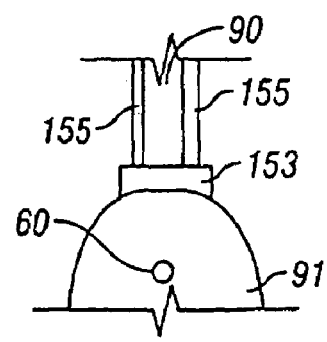
FIG. 11A shows a hook having an insulating sheath according to another embodiment of the invention.

Various portions of the hook 90 or 130 can be sheathed with insulating (e.g., PTFE/Teflon or silicon) tubing or injection molding, leaving exposed only the portion of the hook that is used to cauterize (typically the internal portion of the ankle). The insulating material is advantageous in limiting the electrically active surface area of the tool that is exposed to the surgical environment. If an insulating tubing or molding is provided to insulate, e.g., the proximal portion of the hook, a gasket 153 (e.g., made of low durometer silicon) may be used to cover the exposed portion of the hook between the distalmost portion of the wrist joint (with joint axis 60) of the wrist 91 and the proximal-most portion of the insulating material 155, as shown in FIG. 11A. The gasket 153 prevents a small portion of the metallic hook material (before the insulating material begins) from being undesirably exposed to the surgical environment.

Figure 12A:
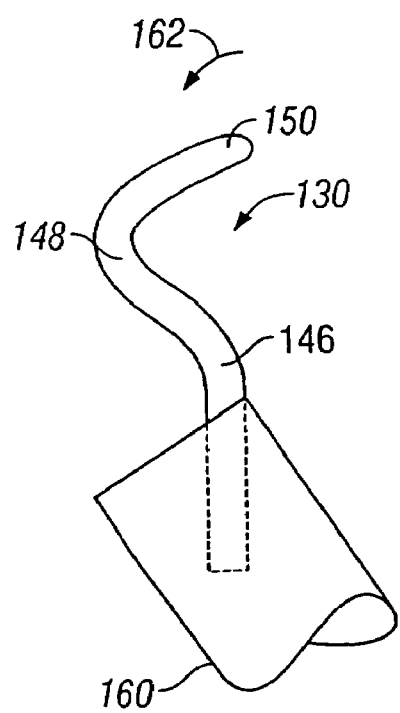
FIGS. 12A-12C illustrate the self-aligning feature of the cautery hook of FIG. 10.
Figure 12B:
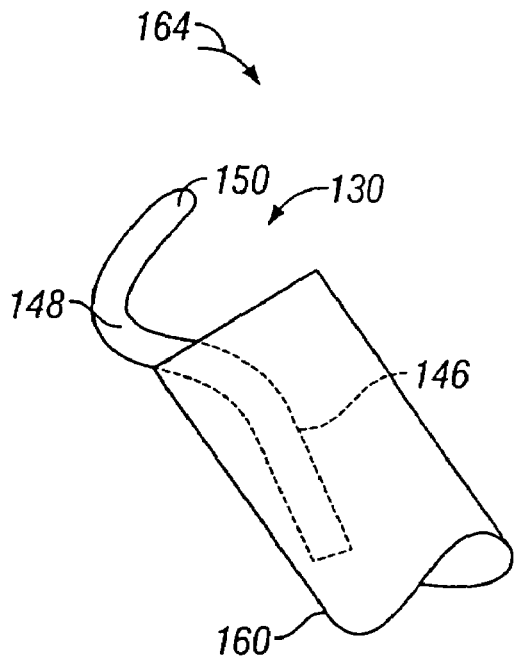
Figure 12C:
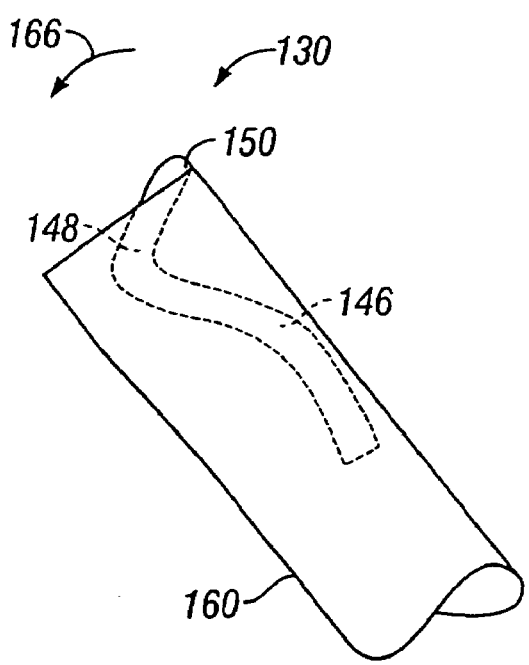

The cautery hooks 90, 130 of FIGS. 8-11 advantageously can self-align as they are passed through a cannula sleeve to avoid getting stuck in the sleeve, to avoid any delay to a surgical procedure during tool exchange, and/or to protect the distal hook portions 114, 144 from being bent or broken off. FIGS. 12A-12C illustrate the self-aligning feature of the cautery hook 130 which is being withdrawn through a cannula sleeve 160. The cautery hook 130 may be mounted on the shaft 14.1 of the surgical instrument 14 (FIG. 3) or connected to a cable or the like when it is passed through the sleeve 160.

In FIG. 12A, the bent knee 146 of the cautery hook 130 contacts the edge of the cannula sleeve 160, causing the hook 130 to rotate in the direction 162 to self-align the hook 130. In FIG. 12B, the ankle 148 produces self-alignment of the cautery hook 130 in the sleeve 160 in the direction 164 when it contacts the sleeve 160. In FIG. 12C, the contact between the distal hook tip 150 and the sleeve 160 causes the cautery hook 130 to self-align with respect to the sleeve 160 in the direction 166. The bent knee 146 is preferably sufficiently forward that sliding engagement between the front surface of the bent knee 46 and the lumen of the cannula sleeve 160 aligns the cautery hook 130 relative to the lumen so as to inhibit interference between the distal hook tip 150 and the cannula when the cautery hook 130 moves proximally into the cannular sleeve 160. Typically, the bent knee 146 coincides with, or extends generally forward of, a plane extending between the proximal end 141 and the distal hook tip 150. In the specific embodiment shown in FIGS. 10 and 11, the proximal portion 140 is generally linear with a longitudinal axis, and the distal hook tip 150 generally coincides with the longitudinal axis extending from the proximal portion 140.

The bent knee 146, ankle 148, and distal hook tip 150 are the three most likely locations of contact between the cautery hook 130 and the cannula sleeve 160. Each contact tends to self-align the hook 130 to allow the hook 130 to pass through the sleeve 160 without getting stuck or damaged. The bent knee 116, ankle 118, and distal hook tip 120 of the cautery hook 90 of FIGS. 8 and 9 provide self-alignment in a similar manner.

Figure 13:
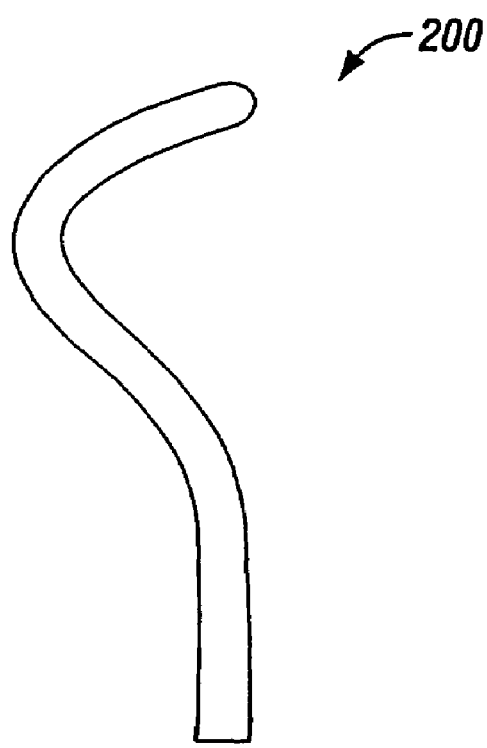
FIGS. 13 and 14 are front and side views of a cautery hook illustrating a sandwiched structure according to another embodiment of the present invention.
Figure 14:
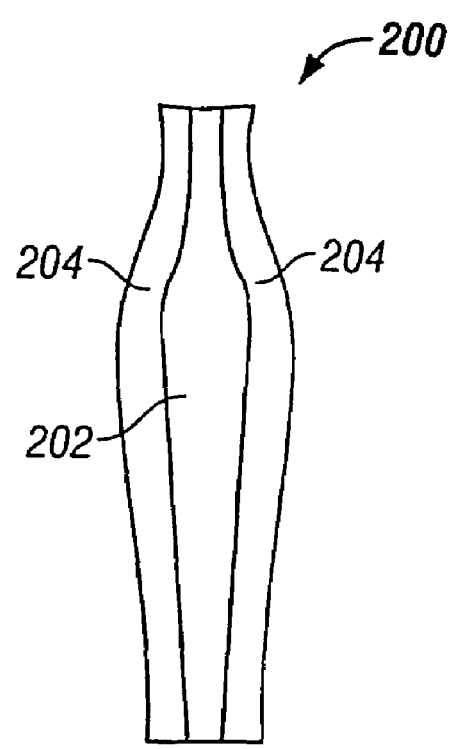

FIGS. 13 and 14 show another hook 200 which can be used as a bipolar cautery hook. The hook 200 includes a sandwiched structure having a core 202 sandwiched between two shell layers or coatings 204. The core 202 includes an insulative material such as ceramic or silicon. The shell layers 204 include a metallic electrode material such as gold (Au). The metallic electrode material may be masked and sputter-deposited so that the deposited metal would not reach around the insulative core 202 to complete an undesired circuit.

It is appreciated that the present invention is not limited to cautery or electrosurgical hooks, but applies, in general, to any hook-shaped instrument that is usable in minimally invasive surgery. Thus, the function required of the hooked structure should not be understood as limiting the invention. For example, hooks that are used to retract tissue that are delivered through a cannula or other tubular delivery device can benefit from the self aligning structure. Other hook structures might be used for dissection, e.g., to hook and then peel the IMA (internal mammary artery) away from the chest wall (instead of having to use scalpel and/or cautery instruments to achieve that function) or for retraction of certain tissues at the surgical site.

It is further appreciated that the hooks having self-aligning features in accordance with the present invention can be of a variety of cross sections, and are not limited to the specific cross sections shown herein.

The above-described arrangements of apparatus and methods are merely illustrative of applications of the principles of this invention and many other embodiments and modifications may be made without departing from the spirit and scope of the invention as defined in the claims. The scope of the invention should, therefore, be determined not with reference to the above description, but instead should be determined with reference to the appended claims along with their full scope of equivalents.

What is claimed is:

1. A surgical instrument, comprising:
a shaft comprising a distal end;
a generally linear proximal portion comprising a proximal end and a distal end, wherein the proximal end of the of the proximal portion is coupled to the distal end of the shaft via a wrist mechanism having at least one degree of freedom;
a generally linear shank portion comprising a proximal end and a distal end, wherein the proximal end of the shank portion is coupled to the distal end of the proximal portion, wherein the shank portion angles away from a front side of the instrument by a knee angle, and wherein the knee angle allows the shank portion to self align and slide without catching into a cannula as the shaft is being withdrawn through the cannula; and
a distal hook portion comprising a proximal end and a tip, wherein the proximal end of the distal hook portion is coupled to the distal end of the shank portion at an ankle, wherein the distal hook portion angles towards the front side of the instrument by an ankle angle, wherein the ankle angle allows the tip to self-align and slide without catching into the cannula as the shaft is being withdrawn through the cannula, and wherein the distal hook portion is configured to receive cauterization energy.

2. The surgical instrument according to claim 1, wherein the shaft comprises a proximal end that is coupled to a housing arranged to releasably couple the instrument to a robot arm.

3. The surgical instrument of claim 1, wherein the proximal portion is coupled to the shaft at a wrist mechanism comprising at least two degrees of freedom.

4. The surgical instrument of claim 3, wherein the shaft comprises a proximal end that is coupled to a housing arranged to releasably couple the instrument to a robot arm.

5. The surgical instrument of claim 1, further comprising an insulator covering at least part of the proximal portion.

6. The surgical instrument of claim 1, wherein the proximal portion, the shank portion, and the distal hook portion are substantially coplanar.

7. The surgical instrument of claim 1, wherein a cross section of the distal hook portion comprises a substantially round shape.

8. The surgical instrument of claim 1, wherein a cross section of the distal hook portion comprises a substantially rectangular shape.

9. The surgical instrument of claim 1, wherein the distal hook portion comprises a generally linear shape.

10. The surgical instrument of claim 1, wherein the distal hook portion comprises an insulating layer sandwiched between two electrode layers.

11. The surgical instrument of claim 1, wherein the shaft comprises a proximal end that is coupled to a housing arranged to releasably couple the instrument to a robot arm.

12. The surgical instrument of claim 1, wherein the tip generally coincides with a longitudinal axis extending from the proximal portion.

* * * * *